United States Patent [19]

Richon et al.

[11] Patent Number: 4,524,611

[45] Date of Patent: Jun. 25, 1985

[54] RHEOMETER FOR MEASURING HIGH PRESSURE AND HIGH TEMPERATURE WITH SAMPLING

[75] Inventors: Dominique Richon, Rosny. Sous. Bois; Henri Renon, Paris, both of France

[73] Assignee: Association pour la Recherche et le Developpement des Methodes et Processus Industriels (ARMINES), Paris, France

[21] Appl. No.: 493,411

[22] Filed: May 10, 1983

[30] Foreign Application Priority Data

May 11, 1982 [FR] France ................. 82 08160

[51] Int. Cl.³ ............................................. G01N 11/14
[52] U.S. Cl. ............................................. 73/59; 73/54
[58] Field of Search ...................... 73/59, 60, 54

[56] References Cited

U.S. PATENT DOCUMENTS 2,484,761 10/1949 Stock ..................................... 73/59
3,435,666 4/1969 Fann ................................. 73/59 X
3,935,729 2/1976 McCarthy ............................. 73/60

*Primary Examiner*—Anthony V. Ciarlante
*Assistant Examiner*—Hezron Williams
*Attorney, Agent, or Firm*—Murray, Whisenhunt & Ferguson

[57] ABSTRACT

Rheometer for effecting measurement of rheological properties in a medium, comprising a hollow body (2) having an inner chamber (3) with a lower zone (3A) and an upper zone (3B) of enlarged diameter. An inner shaft (9) is located in the inner chamber (3) and is driven by a magnetic coupling (12A-13) through a cap (4) for hermetically sealing the hollow body (2). A rotor (18) is provided on the inner shaft (9) and is displaceable in a longitudinal direction between an upper position where it is located in the upper zone (3B) and a lower position where it is located in its position for measurement. A stirrer (10-11) is keyed to the lower part of the inner shaft (9) and is receivable within the rotor (18).

12 Claims, 2 Drawing Figures

RHEOMETER FOR MEASURING HIGH PRESSURE AND HIGH TEMPERATURE WITH SAMPLING

Rheometer incorporating cylinders for effecting measurements under high pressure and temperature with sampling.

The invention relates to a rheometer of the type incorporating cylinders especially adapted to effect measurements of rheological properties in a medium in which the homogeneity must be maintained with certainty and which is adapted to be held under pressure and taken to a high temperature.

Reference will hereinafter be made to a rheometer which allows measurements up to a pressure of 300 bars and a temperature of 550° C. Of course, this apparatus may be used at any lower value of the pressure and temperature; in addition, as will appear hereinafter, its design renders it capable of serving at higher values, the figures mentioned being in no way limiting.

Such a rheometer is necessary in the course of certain research such as that directed to the hydroliquefaction of products such as coal, ligneous matters or heavy residues of oil. This operation is carried out by a hydrogenation in liquid phase: pulverized product (for example coal) is mixed with oil to yield a paste which is circulated in a series of reactors under hydrogen pressure, with the temperature being progressively increased during passage through the reactors.

It is therefore necessary to know how the viscosity of the liquid phase varies as a function of the temperature.

One difficulty arises from the necessity of maintaining in the liquid phase a sufficient concentration of hydrogen, in particular in the air gap of the rheometer between the fixed cylinder and the rotating cylinder. This is because an insufficient concentration of hydrogen in the suspension of coal leads to a coking process, and therefore to a setting of the mass having a low hydrogen concentration.

The main object of the invention is to provide a rheometer incorporating cylinders which allows measurements of rheological properties in a medium of which the homogeneity is well conserved, and in which the risk of mass setting in the air gap of the medium subjected to the measurement as in the case of hydrogenation of the coal mentioned above, at various conditions of temperature and pressure, is reduced.

However, in the case of hydroliquefaction of the coal, it is also very useful to know the composition of the liquid phase and of the vapour phase at the moment when measurement is effected.

It is a further object of the invention to produce a rheometer incorporating a rotor with which samplings of liquid phase and of vapour phase are possible just before or after effecting a measurement of viscosity, without disturbing this measurement.

A rheometer according to the invention comprises a pressure-resistant hollow body, open at its upper end and covered with a dismountable cap which, after being positioned on the body, ensures the hermetic closure of the latter. An inner vertical shaft is mounted in the body and held by its ends in appropriate bearings: at its top, this shaft is provided with radially spaced magnets and magnets are borne in register by an outer shaft, above the cover, to constitute a magnetic coupling.

The inner volume or inner chamber of the hollow body comprises a lower zone constituting a fixed measuring cylinder and an upper zone of enlarged diameter with respect to the lower zone whose height is at least equal to that of the rotating cylinder or measuring rotor. The rotor is mounted on the inner shaft and is capable of longitudinal displacement between an upper position where it is located in the upper zone and a lower position where it is located in the lower zone and where it radially limits an air gap with the fixed cylinder, in manner known per se.

Means are provided for displacing the rotor along the inner shaft. These means are preferably associated with the rotor and with the inner shaft.

The rotor is preferably also hollow and it has an inner diameter which enables it to contain a stirrer also mounted on the inner shaft. This stirrer may be mobile in displacement with the rotor along the inner shaft.

In one embodiment of the invention, the stirrer is keyed in rotation and in translation on the vertical shaft, in the lower zone of the inner volume.

The means for longitudinal displacement of the rotor preferably comprise a thread provided on the inner shaft and a nut incorporated in the rotor.

The direction of the thread is such that, when the inner shaft is rotated in direction opposite the direction of execution of the measurements of viscosity, the nut is screwed on this shaft and the rotor rises into the upper zone, totally leaving the zone of the air gap. In this way, the rotor is displaceable between a lower position where it serves to execute the measurements of rheological properties and an upper position in which it no longer serves to limit the air gap.

In the wall of the lower zone of the hollow body is drilled a hole in which is mounted a needle pushed against a seat close to the inner face of the hollow body. In the lateral face of this needle, to the rear of its head, is hollowed a groove in register with two spaced apart channels which extend laterally through the wall of the hollow body up to its outer face.

The needle is preferably applied against the seat by a compressible elastic element to allow its opening.

In the wall of the upper zone of the hollow body is hollowed a lateral chamber from which is drilled a hole containing a valve of which the seat is the orifice of this hole opening into this lateral chamber. To the rear of its head, the rod of the valve has in its lateral face a groove placed in register with two spaced apart channels which extend laterally through the wall of the hollow body up to its outer face.

The valve is preferably applied against its seat by a compressible elastic element to allow its opening.

A description of an embodiment of the invention will now be given solely by way of example and without any limiting intention. Reference will be made to the accompanying drawings, in which.

Figure 1:
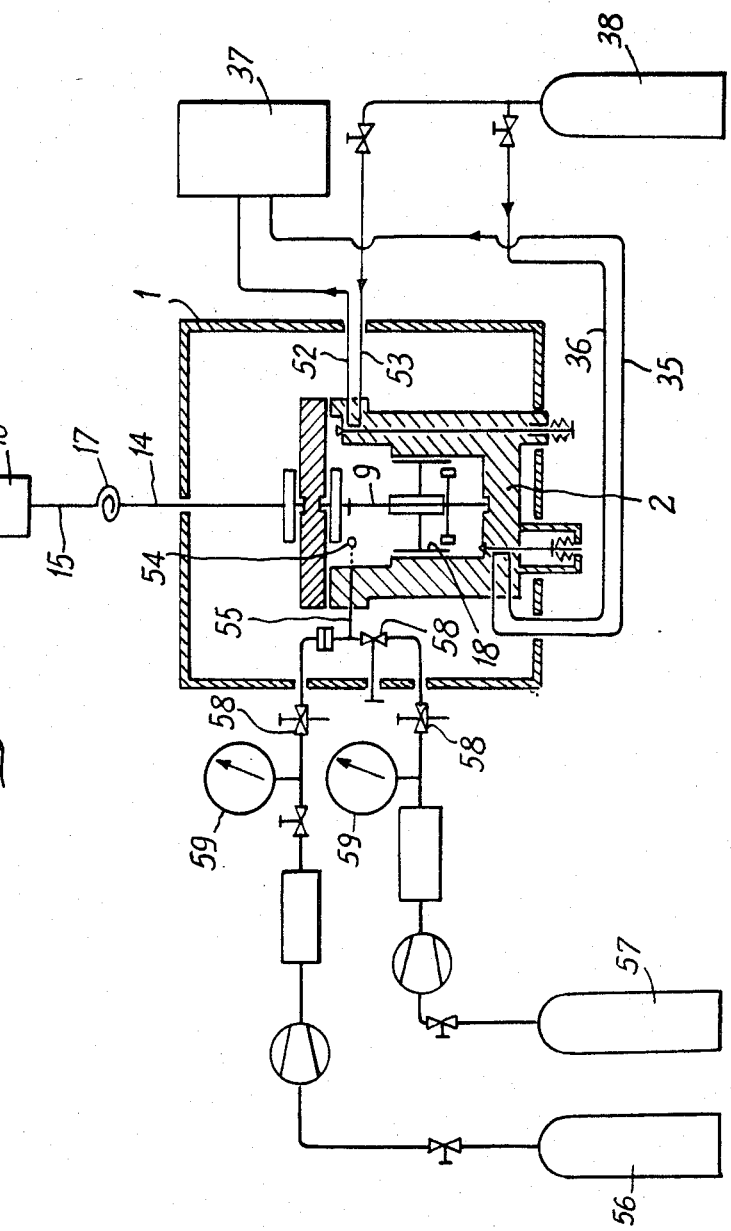
FIG. 1 is a schematic representation of the whole of a measuring installation comprising a rheometer according to the invention.
Figure 2:
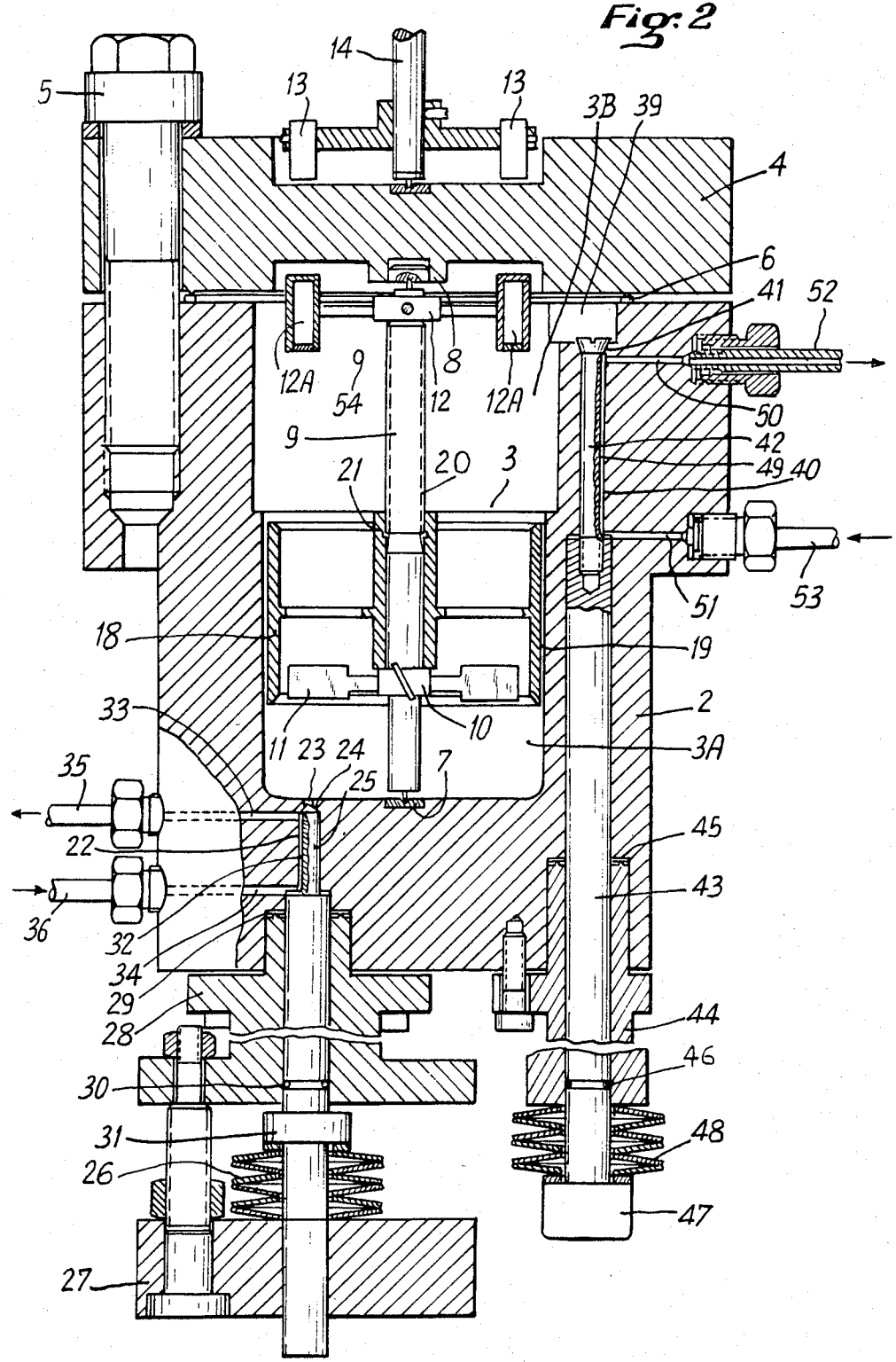
FIG. 2 is an enlarged view in section through a plane passing through the axis of the rheometer of FIG. 1.

The rheometer of the invention is disposed inside an enclosure 1 at constant temperature around which different peripheral apparatus are located.

It comprises a hollow body 2 having an inner chamber 3 in which are distinguished a lower zone 3A which serves as fixed cylinder and an upper zone 3B of enlarged diameter, with an upper opening which may be hermetically closed due to a cap 4. The latter is held in place by screws 5 which enable an O-ring 6 ensuring tightness to be crushed.

In the bottom of the inner chamber 3 is provided a bearing 7 and in the cap 4 a bearing 8 which maintain in the axis of the hollow body 1 and of the inner chamber 3 a vertical inner shaft 9. In its lower part, substantially one third of the way up from the bottom of the lower zone 3A of the inner chamber 3, the inner shaft 9 is provided with a stirrer 10 incorporating blades 11, keyed in rotation and in longitudinal displacement. At its top, the inner shaft 9 is provided with a hub 12 which bears a plurality of magnets 12A spaced apart radially and circularly below the cap 4. Above the latter are mounted, in register, magnets 13 borne by an outer shaft 14. In this way, a magnetic coupling in rotation is obtained through the cap 4 which is made of suitable material. The magnets are preferably made of TICONAL so as to conserve good magnetic properties at 550° C. The outer shaft 14 is itself coupled in rotation to the shaft 15 of a motor 16 via a spiral spring 17 associated with a read off scale (not shown) for measuring the drive torque of the inner shaft 9.

A hollow rotating cylinder or rotor 18 is mounted on this inner shaft 9 with a possibility of displacement in longitudinal direction between a lower position and an upper position.

In its upper position, the rotor 18 is totally included in the upper zone 3B of enlarged diameter whose height is at least equal to that of the rotor. In its lower position, the rotor 18 is included in the lower zone 3A where the hollow body serves as fixed cylinder and limits with the rotor 18 an air gap 19, as is known in viscometers incorporating a rotating cylinder.

Displacement of the rotor 18 may be effected by any appropriate means; in this example, the upper part of the inner shaft 9 bears a thread 20 and the rotor 18 comprises a nut 21. The direction of the thread is such that, when the shaft 9 is driven rapidly in rotation in direction opposite the direction of rotation of the measurement of viscosity, the nut 21 screws on the thread 20 and the rotor 18 rises to its upper position until it encounters the hub 12. The lower zone 3A which serves as fixed cylinder is totally cleared, with the exception of the stirrer 10 which remains in place and which creates a strong stirring in the liquid phase located there.

When rotation is effected in the direction of measurement, the rotor 18 descends into the lower zone 3A until it encounters the hub of the stirrer 10. The air gap 19 is then established and measurement may be effected in a homogeneous phase. The stirrer which has a diameter smaller than the inner diameter of the hollow rotor 18 is then included in the latter.

In the bottom wall of the hollow body 2 is drilled a channel 22 terminating in the inner chamber 3 in a smaller orifice 23 so as to form a seat 24 for a needle 25 which extends outwardly and which is pushed into position of closure by a plurality of elastic washers 26 retained by a clamp 27. The needle 25 is mounted to slide in a stopper 28 which crushes an annular seal 29 and it is surrounded by an O-ring 30. An enlargement 31 is provided on the needle 25 outside the stopper 28 to serve as bearing surface for the elastic washers 26 and to enable it to be manoeuvred in the direction of opening against the thrust thereof.

To the rear of its head associated with the seat 24, the needle 25 has, in its lateral face, a longitudinal groove 32 opposite which two spaced apart transverse channels 33, 34 are pierced through the wall of the hollow body 2 up to its outer face for connection to two tubes 35, 36 which respectively terminate in an apparatus for analysis 37 and a source of fluid 38.

At the top of the inner chamber 3 is made in the thickness of the wall a lateral chamber 39 in which opens out a hole 40 drilled in longitudinal direction from the lower outer face of the hollow body 2. The orifice of the hole 40 serves as seat 41 for a valve 42 extended by a spindle 43 which slides in a stopper 44. This latter crushes an annular seal 45 and contains an O-ring 46 which render the assembly of the spindle 43 tight. The latter terminates in an enlargement 47 for retaining elastic washers 48 which abut against the stopper 44.

To the rear of the seat 41 of the valve 42, the rod of the latter has a longitudinal groove 49 and two spaced apart transverse channels 50, 51 are pierced through the wall of the hollow body 2 to allow their connection to two tubes 52, 53 which respectively terminate in the apparatus for analysis 37 and the source of fluid 38.

A transverse hole 54 is pierced through the wall at the level of the upper zone 3B of the inner chamber 3; it is connected to a tube 55 which terminates at two sources of pressurized gas 56, 57 and on which are located valves 58 and pressure gauges 59. The desired gases are therefore easily introduced into the hollow body 2 to establish the desired pressure therein, after having filled it with solid substance and having hermetically closed the cap 4.

Any measurement of rheological property may be preceded by a period of homogenization of the phase or of the mixture of phases contained in the lower zone 3A, with the aid of the stirrer 10 whilst the rotor 18 occupies its upper position, as explained hereinabove.

Sampling may be made at any moment, in the upper zone 3B and in the lower zone 3A. It suffices to pull the needle 25 or raise the valve 42 for a very brief period: a percussion produced in the desired direction is sufficient. The sample which escapes fills the groove 32 or 49. A fluid serving as vector is sent via one of the transverse channels 34 or 51 and collected with the sample via the other of the transverse channels 33 or 50, coming from the source of fluid 38 up to the apparatus 37 for analysis.

An apparatus as described hereinabove is very useful for determining the quantities necessary for creating processes operating at high temperature and/or high pressure.

We claim:

1. A rheometer, including a hollow body (2) with an inner chamber (3), a cap (4) for closure of the hollow body (2), a vertical inner shaft (9), a rotor (18) mounted on the inner shaft (9), and means for rotating the inner shaft (9) via a torque measuring means, characterized in that said inner chamber (3) comprises a lower zone (3A) constituting a fixed measuring cylinder, and an upper zone (3B) having an enlarged diameter with respect to the lower zone (3A), and having a height at least equal to that of said rotor (18), said rotor (18) being displaceable in a longitudinal direction along said inner shaft (9) between an upper position in which said rotor (18) is located in said upper zone (3B) and a lower position in which said rotor (18) is located in said lower zone (3A) for effecting a measurement.

2. A rheometer according to claim 1, characterized in that said rotor (18) is hollow, and said inner shaft (9) is provided in said lower zone (3A) with a stirrer (10) keyed in rotation, said stirrer (10) having a diameter smaller than the inner diameter of said hollow rotor (18) so that said stirrer (10) may be received within said rotor (18).

3. A rheometer according to claim 2, characterized in that said stirrer (10) is keyed in translation in the lower part of said inner shaft (9) contained in said lower zone (3A).

4. A rheometer according to claim 1, characterized in that means for effecting translational displacement of said rotor (18) are associated with said rotor (18) and with said inner shaft (9).

5. A rheometer according to claim 4, characterized in that said means for effecting translational displacement of said rotor (18) comprise a thread (20) provided on said inner shaft (9) in a part of said inner shaft (9) located in said upper zone (3B) and a nut (21) fixed to said rotor (18), the direction of said thread (20) being such that a rotation in a direction opposite to the direction of rotation for effecting a measurement causes displacement of said rotor (18) to said upper position.

6. A rheometer according to claim 1, 2, 3, 4 or 5 characterized in that said inner shaft (9) is provided at its top with a hub (12) bearing magnets (12A) beneath the cap (4), said magnets (12A) being associated with magnets (13) mounted above the cap (4) on an outer shaft (14) to provide a magnetic coupling through the cap (4).

7. A rheometer according to claim 6, characterized in that said hub (12) serves as a stop for said rotor (18) in its upper position and said stirrer (10) serve as stop for said rotor (18) in its lower position, said stirrer (10) then being contained in said rotor (18).

8. A rheometer according to claim 1, 2, 3, 4, 5 or 7, characterized in that a hole (22) is provided in a wall of said hollow body (2), said hole (22) opening out in said lower zone (3A) through a narrow orifice (23) to form a seat (24) for a needle (25) pushed by a compressible elastic element (26), for taking samples.

9. A rheometer according to claim 1, 2, 3, 4, 5 or 7, characterized in that a hole (40) is provided in a wall of said hollow body (2), said hole (40) opening out in said upper zone (3B) to provide a seat (41) for a valve (42) seated on said seat (41) by a compressible elastic element (47), for taking samples.

10. A rheometer according to claim 9, characterized in that said hole (40) opens out in a chamber (39) located laterally with respect to said upper zone (3B).

11. A rheometer according to claim 8, characterized in that a longitudinal lateral groove (32) is in communication with said seat (24), and is in register with two spaced apart transverse channels (33), (34) connected to a source of fluid (38) and to a measuring apparatus (37).

12. A rheometer according to claim 9, characterized in that a longitudinal lateral groove (49) is in communication with said seat (41) and is in register with two spaced apart transverse channels (50), (51) connected to a source of fluid (38) and to a measuring apparatus (37).

* * * * *